(12) United States Patent
Harima et al.

(10) Patent No.: US 7,759,505 B2
(45) Date of Patent: Jul. 20, 2010

(54) METHOD OF PRODUCING FATTY ACID ESTER

(75) Inventors: Kazuyuki Harima, Wakayama (JP); Hidetoshi Kadowaki, Wakayama (JP); Taku Mimura, Wakayama (JP)

(73) Assignee: Kao Corporation, Tokyo (JP)

( * ) Notice: Subject to any disclaimer, the term of this patent is extended or adjusted under 35 U.S.C. 154(b) by 146 days.

(21) Appl. No.: 11/657,452

(22) Filed: Jan. 25, 2007

(65) Prior Publication Data

US 2007/0191650 A1 Aug. 16, 2007

(30) Foreign Application Priority Data

Jan. 27, 2006 (JP) ............................ 2006-018596
Nov. 9, 2006 (JP) ............................ 2006-304242

(51) Int. Cl.
*C11B 3/00* (2006.01)

(52) U.S. Cl. ...................................... 554/191; 568/884

(58) Field of Classification Search ....................... None
See application file for complete search history.

(56) References Cited

U.S. PATENT DOCUMENTS 5,120,885 A 6/1992 Tsukada et al.
6,524,994 B1 * 2/2003 Reesink et al. ............... 502/337
2003/0225304 A1 * 12/2003 Mumura et al. .............. 568/885

FOREIGN PATENT DOCUMENTS

| EP | 0985448 A1 | 3/2000 |
|---|---|---|
| JP | 05-000978 * | 1/1993 |
| JP | 5-978 A | 1/1993 |
| JP | 05000978 * | 1/1993 |
| JP | 6-57286 A | 3/1994 |
| JP | 2000-42413 A | 2/2000 |
| JP | 2000-79343 A | 3/2000 |
| JP | 2002-523230 A | 7/2002 |
| WO | WO-02/100541 A1 | 12/2002 |

* cited by examiner

*Primary Examiner*—Deborah D Carr
(74) *Attorney, Agent, or Firm*—Birch, Stewart, Kolasch & Birch, LLP

(57) ABSTRACT

The present invention relates to a method of producing a fatty acid ester, including treating a starting fatty acid ester with an adsorbent to adsorb sulfur contained in the starting fatty acid ester, the adsorbent containing at least one metal selected from Ni and Cu in an amount of 10 to 85 percent by weight as a metal oxide(s) thereof per all the adsorbent, having a pore volume having a pore diameter range from 20 to 200 nm within 0.15 to 1.0 mL/g and then a method of producing an alcohol, including hydrogenating a fatty acid ester obtained by the above shown method of producing a fatty acid ester.

12 Claims, No Drawings

METHOD OF PRODUCING FATTY ACID ESTER

FIELD OF THE INVENTION

The present invention relates to a method of producing a fatty acid ester and a method of producing an alcohol from the fatty acid ester obtained in this production method.

BACKGROUND OF THE INVENTION

Fatty acid esters usually contain sulfur in a content of at least several milligrams/kg to several tens of milligrams/kg. Here, the fatty acid ester means esters of fatty acids and glycerin (triglycerides, diglycerides and monoglycerides) or esters of fatty acids and alcohols having 1 to 22 carbon atoms (fatty acid alcohol esters) and partly contains free fatty acid depending on the case. When these fatty acid esters are allowed to undergo a hydrogenation reaction in the presence of an ester reduction catalyst to produce alcohols, sulfur contained in the fatty acid esters acts as catalyst poison of a hydrogenation catalyst to significantly deteriorate the catalyst activity.

In the case of, particularly, a fixed-bed continuous reaction, the life of the catalyst is very shortened, which requires frequent exchanges of the catalyst, so that a reduction in the rate of operation is unavoidable.

Also, the fatty acid ester is known as a light gas oil substitute used for bio-diesel fuel and there is demand for fatty acid esters reduced in the content of sulfur in such an application from the viewpoint of reducing sulfur oxides in exhaust gas.

Therefore, various studies have been made so far with the intention of removing sulfur which is to be a catalyst poison of hydrogenation catalysts. For example, methods reducing the content of sulfur by distillation are frequently used because sulfur compounds have relatively higher boiling points. However, it is impossible to remove all sulfur compounds by distillation. Also, in order to decrease the concentration of sulfur to a level as low as 0.5 mg/kg, it is necessary to dispose of a large amount of originally necessary high-boiling components with a remarkable reduction in yield.

Also, in petrochemical fields, a desulfurization catalyst containing, as major components, molybdenum, cobalt and nickel is used. In order to make these catalysts develop desulfurization activity, a reaction temperature of 300° C. or more is necessary. In order to improve desulfurization activity, an attempt is made to define the pore volume having a pore diameter of 6 to 9 nm or 7 to 12 nm (JP-A 2000-42413 and JP-A 2000-79343). The reaction temperature should be 300° C. or more.

In the meantime, a method is disclosed in which a sulfur compound is hydrocracked in a hydrogen atmosphere to adsorb the sulfur compound by using an adsorbent containing a metal such as Ni or Cu (JP-A 5-978 and JP-A 5-57286).

Also, JP-A 2002-523230 discloses a nickel catalyst which contains 87.5 to 99.9 percent by weight of nickel and may be used for desulfurization of a solvent.

SUMMARY OF THE INVENTION

The invention provides a method of producing a fatty acid ester, including treating a starting fatty acid ester with an adsorbent to adsorb sulfur contained in the starting fatty acid ester, the adsorbent containing at least one metal selected from Ni and Cu in an amount of 10 to 85 percent by weight as a metal oxide(s) thereof per all the adsorbent, having a pore volume having a pore diameter range from 20 to 200 nm within 0.15 to 1.0 mL/g.

The invention provides a method of producing an alcohol, including hydrogenating a fatty acid ester obtained by the above shown method of producing a fatty acid ester.

DETAILED DESCRIPTION OF THE INVENTION

The adsorbents of JP-A 5-978 and JP-A 6-57286 have an insufficient activity and in order to maintain the adsorbing ability to be intended, it is necessary to exchange an expensive adsorbent frequently or to install a large-scale adsorbing apparatus, posing a problem concerning high adsorbing cost.

In the JP-A 2002-523230, the content of metals such as nickel is excessive, there is the case where the strength of an adsorbent is reduced by the generation of voids caused by reduction. Therefore, it is difficult to secure sufficient strength when a molded adsorbent is packed and there is also a fear as to the generation of dusts.

The present invention provides a method of producing a fatty acid ester reduced in the content of sulfur and to a method of producing an alcohol by using a fatty acid ester obtained in the above production method as a starting material.

The inventors of the present invention have made earnest studies to solve the above problem and as a result, found that an adsorbent which contains at least one type selected from Ni and Cu in a specified amount and has a specified porous structure is highly active as a desulfurization catalyst for a fatty acid ester and is useful for the production of an fatty acid ester having a low sulfur content.

According to the present invention, a fatty acid ester reduced in the content of sulfur can be obtained and, further, an alcohol can be efficiently produced using the fatty acid ester as a starting material.

[Starting Fatty Acid Ester]

Examples of the starting fatty acid ester used in the present invention include ester of fatty acids and glycerin (triglyceride, diglyceride and monoglyceride) and esters of fatty acids and alcohols having 1 to 22 carbon atoms (fatty acid alcohol esters). Examples of the glycerides among these compounds include animal triglycerides such as tallow and fish oils, vegetable triglycerides such as palm kernel oil, coconut oil, palm oil, soybean oil and rapeseed oil and diglycerides and monoglycerides derived from these compounds. Among these compounds, those having fatty acids having 8 to 22 carbon atoms as their structural fatty acids are preferable and particularly, those derived from vegetable glycerides are preferable.

Also, the fatty acid alcohol ester may be obtained by an ester exchange reaction between the above glycerides and alcohols having 1 to 22 carbon atoms or an esterification reaction between fatty acids derived from the above glycerides and alcohols having 1 to 22 carbon atoms. As the alcohols to be used, lower alcohols having 1 to 4 carbon atoms are preferable.

The ester exchange reaction and the esterification reaction may be run by a known method. Though the reaction may be run using any of reaction systems, for example, a continuous system and a batch system, the continuous reaction system is advantageous when a large amount of the ester is produced. As the catalyst, though homogenous alkali catalysts such as sodium hydroxide, potassium hydroxide and sodium alcoholate are usually used, solid catalysts such as ion exchange resins, hydrate zirconium hydroxide, aluminum phosphate, sulfuric acid-carrying zirconia and titanosilicate may be used. When using the homogenous alkali catalyst, the reaction is usually run in the following condition. The reaction temperature is 30 to 90° C. and preferably 40 to 80° C., the reaction pressure is in a range from normal pressure to 0.5 MPa and preferably normal pressure under which the reaction is run. Also, the molar amount of the alcohol is preferably 1.5 to 10 times as much as the molar amount of the glycerides from the viewpoint of cost and reactivity. Also, when a free fatty acid is contained in the glycerides, it is effective to esterify the fatty acid in advance by using an acid catalyst such as sulfuric acid or paratoluenesulfonic acid prior to the interesterification with an alkali catalyst.

As the starting fatty acid ester, those having a sulfur content of preferably 50 mg/kg or less, more preferably 30 mg/kg or less and even more preferably 10 mg/kg or less before processed may be used.

Examples of sulfur-containing compounds which can be efficiently removed by the adsorbent of the present invention include aromatic sulfur-containing compounds such as thiols, sulfides, disulfides, thiocarboxylic acids and thiophene.

[Adsorbent]

The adsorbent used in the present invention is one which contains at least one metal selected from Ni and Cu in an amount of 10 to 85 percent by weight as a metal oxide(s) thereof per all the adsorbent and in which the pore volume having a pore diameter range from 20 to 200 nm is 0.15 to 1.0 mL/g. At least one metal selected from Ni and Cu is preferably carried on a support.

The content of the metal in the adsorbent is 10 percent by weight or more, preferably 30 percent by weight or more, even more preferably 40 percent by weight or more and even more preferably 50 percent by weight or more from the viewpoint of adsorbing capacity. Also, the content of the metal is 85 percent by weight or less and preferably 80 percent by weight or less from the viewpoint of the strength of the adsorbent.

The content of a nickel metal in the adsorbent is preferably 30 percent by weight or more, more preferably 40 percent by weight or more and even more preferably 50 percent by weight or more from the viewpoint of adsorbing capacity. Also, the content of a nickel metal is preferably 80 percent by weight or less from the viewpoint of the strength of the adsorbent.

The metal content so called here is an amount as a metal oxide(s) per all the adsorbent containing a metal(s), a support, a binder and other components.

As the support, a known support such as silica, alumina, silica alumina, zeolite, diatomaceous earth, activated clay, titania, zirconia and activated carbon may be used. Among these compounds, silica, alumina, silica alumina, titania and zirconia are preferable, and silica and silica alumina are more preferable.

There is no particular limitation to a method of supporting at least one metal selected from Ni and Cu, and a co-precipitation method, impregnation method, uniform kneading method or the like may be applied. Also, a combination of these preparation methods may be applied. In the case of, for example, a co-precipitation method, a method may be utilized in which an aqueous solution in which any one or more of a water-soluble Ni salt and water-soluble Cu salt, an aqueous solution containing a material used as the support and an aqueous alkali metal solution are mixed to precipitate the metal and the support simultaneously and the resulting precipitate is washed, dried and baked. Also, in the case of an impregnation method, a method may be utilized in which a support powder is impregnated with an aqueous solution in which any one or more of a water-soluble Ni salt or a water-soluble Cu salt is dissolved, followed by drying and baking.

As the shape of the adsorbent, an appropriate one may be selected from a powder form, granular form, and shapes such as a sphere form and columnar form obtained by molding, according to the type of adsorption treating systems and the structure of a reactor. A granular form or molded shapes are preferable from the viewpoint of reducing the pressure drop when a fluid is passed through the adsorbent.

Each of these adsorbents is usually used after it is reduced and activated by hydrogen. Also, an adsorbent which is subjected to reducing and activating treatment and stabilizing treatment in advance may be used as it is or after it is reduced and activated again.

The pore structure of the adsorbent can be controlled by variously changing a catalyst preparation conditions such as a precipitation condition, drying condition, molding condition and baking condition. The starting fatty acid ester used in the present invention is a molecule which which is more polar and bulkier than kerosene and light gas oil used in petrochemical fields and therefore, the technologies used in petrochemical fields cannot be used as it is. The adsorbent used in the present invention is one having a specific pore distribution so that it can be used for desulfurization of the starting fatty acid ester. Specifically, pores having a diameter ranging from 20 to 200 nm are effective for the desulfurization reaction of the starting fatty acid ester and an adsorbent having a high desulfurization activity can be obtained by controlling the pore volume having a diameter falling in this range. The pore volume having a diameter range from 20 to 200 nm is 0.15 mL/g or more, preferably 0.20 mL/g or more and more preferably 0.25 mL/g or more from the viewpoint of developing sufficient desulfurization activity. Also, in the case of using the adsorbent as a molded article, the bulk density is preferably high from the viewpoint of enabling the reactor to be designed to be compact and therefore, the pore volume having a diameter ranging from 20 to 200 nm is 1.0 mL/g or less and preferably 0.7 mL/g or less.

The mode diameter of the pore diameter of the adsorbent of the present invention is preferably 20 nm or more and more preferably 30 nm or more from the viewpoint of developing sufficient desulfurization activity. The mode diameter is preferably 200 nm or less and more preferably 100 nm or less from the viewpoint of the strength of the adsorbent.

It is to be noted that the pore volume and pore diameter to be used in the present invention is measured by a mercury porosimetry method. The maximum pressure in the mercury porosimetry method is designed to be 207 MPa to measure pores having a diameter of 6 nm or more.

[Method of Producing a Fatty Acid Ester]

The method of producing a fatty acid ester according to the present invention is a method in which the starting fatty acid ester obtained in the above manner is subjected to the sulfur adsorption treatment using the aforementioned adsorbent to produce a fatty acid ester reduced in the content of sulfur. It is effective to carry out distillation for the purpose of removing impurities and further reducing the concentration of sulfur before or after carrying out the adsorption treatment.

As the adsorption treating system, any of the usually used systems such as a suspension, system and fixed-bed system may be used. In the case of treating the fatty acid ester in a large amount, a continuous fixed-bed system is advantageous.

In the case of carrying out adsorption treatment continuously in a fixed-bed system, the treatment is preferably carried out in the following condition. Hydrogen is preferable as the atmospheric gas and inert gas may be allowed to coexist. Examples of the inert gas include nitrogen, argon, helium and methane. As to the flow rate of the atmospheric gas, the molar ratio of hydrogen to the starting fatty acid ester is preferably in a range from 0.1 to 300. The pressure of the atmospheric gas is preferably 0.01 to 50 MPa and more preferably 0.1 to 30 MPa.

The treating temperature is preferably 40° C. or more and more preferably 50° C. or more from the viewpoint of obtaining sufficient adsorption rate. Also, the treating temperature is preferably 200° C. or less and more preferably 180° C. or less from the viewpoint of suppressing side reactions such as hydrocracking.

The flow rate of the starting fatty acid ester is 0.1 or more in terms of liquid hourly space velocity (LHSV) and 5 or less in terms of LHSV from the viewpoint of obtaining sufficient adsorption ability though it is properly designed in view of productivity, catalyst life, limitation to hydrocracking.

The sulfur adsorption treatment like the above ensures can be reduced to 2 mg/kg or less when the starting fatty acid ester is glycerides and to 0.6 mg/kg or less when the starting fatty acid ester is a fatty acid alcohol ester. When the fatty acid ester which has been subjected to the adsorption treatment is used as a starting material in the production of an alcohol, a drop in activity caused by hydrogenation catalyst poison is reduced and is therefore useful. The concentration of sulfur of the glycerides after the adsorption treatment is preferably 1.7 mg/kg or less and more preferably 1.5 mg/kg or less. The concentration of sulfur in the fatty acid alcohol ester after the adsorption treatment is preferably 0.3 mg/kg or less, more preferably 0.25 mg/kg or less and even more preferably 0.20 mg/kg or less.

[Method of Producing an Alcohol]

The method of producing an alcohol according to the present invention is a method in which a fatty acid ester having a small sulfur content which is produced in the above method is used as a starting material to run a hydrogenation reaction.

As the hydrogenation catalyst, a generally known copper type and catalysts of precious metals such as palladium and platinum are used. Examples of the copper type catalyst may include copper-chromium, copper-zinc, copper-iron-aluminum and copper-silica. The hydrogenation reaction may be run under the presence of any of the above catalysts even by any of the usually used reaction systems such as a liquid phase suspension bed system and a fixed-bed system.

In the case of running the reaction by a liquid phase suspension bed system, the amount of the catalyst is preferably 0.1 to 20 percent by weight based on the fatty acid ester. An appropriate amount of the catalyst may be optionally selected corresponding to the reaction temperature or reaction pressure within the range in which practical reaction yield is obtained. The reaction temperature is preferably 160 to 350° C. and more preferably 200 to 280° C. The reaction pressure is preferably 0.1 to 35 MPa and more preferably 3 to 30 MPa.

As the catalyst in the case of running the reaction continuously in a fixed-bed system, a catalyst molded into a cylindrical form, pellet form or spherical form is used. The reaction temperature is preferably 130 to 300° C. and more preferably 150 to 270° C. and the reaction pressure is preferably 0.1 to 30 MPa. The LHSV is optionally determined corresponding to the reaction condition taking productivity and reactivity into account.

EXAMPLES

The present invention is described by reference to the Example below. The Examples are provided for mere illustration of the present invention and not intended to limit the present invention.

In the following examples, the concentration of sulfur was measured by a low-concentration sulfur analyzer 9000 LLS manufactured by ANTEK. The pore diameter and the pore volume were measured by a Pore Sizer 9320 manufactured by Micromeritics.

Preparation Example of a Starting Fatty Acid Ester 0.3 percent by weight of NaOH and 10 percent by weight of methanol were added to palm kernel oil while removing produced glycerin phase in three lots to react the mixture at 50° C. for 3 hours. After the reaction, the oil phase was washed with water to obtain palm kernel oil fatty acid methyl ester. The obtained palm kernel oil fatty acid methyl ester was further treated by distillation to obtain a palm kernel oil fatty acid methyl ester having a sulfur concentration of 1.0 mg/kg. In the following examples, this fatty acid methyl ester was used as the starting fatty acid ester.

Production Example 1 of an Adsorbent

A 2 L separable flask was charged with 800 g of ion exchange water and 232 g of $Ni(NO_3)_2.6H_2O$ and the mixture was raised to 80° C. with stirring. A solution obtained by dissolving 33 g of JIS No. 3 water glass and 113 g of $Na_2CO_3$ in 630 g of ion exchange water and by heating the mixture to 80° C. was poured into the flask with stirring. After the solution was poured, 24 g of $Mg(NO_3)_2.6H_2O$ was added to the mixture. The produced slurry was stirred at 80° C. for one hour and then subjected to filtration and washing with water, followed by drying at 110° C. to obtain a precursor. Then, the precursor was molded into a noodle form by using alumina as a binder, and then, baked, reduced and stabilized to obtain an adsorbent A having a diameter of 1.6 mm. The pore volume having a pore diameter ranging from 20 to 200 nm in the adsorbent A was 0.361 mL/g.

Production Example 2 of an Adsorbent

A 2 L separable flask was charged with 840 g of ion exchange water, 180 g of $Ni(NO_3)_2.6H_2O$, 22 g of $Cu(NO_3)_2.3H_2O$, 4 g of γ-alumina and 4.7 g of 60 percent nitric acid and the mixture was raised to 80° C. with stirring. A solution obtained by dissolving 50 g of JIS No. 3 water glass and 118 g of $Na_2CO_3$ in 570 g of ion exchange water and by heating the mixture to 80° C. was poured into the flask with stirring. The produced slurry was stirred at 80° C. for one hour and then subjected to filtration and washing with water, followed by drying at 110° C. to obtain a precursor. Then, the precursor was molded into a noodle form by using alumina as a binder, and then, baked, reduced and stabilized to obtain an adsorbent B having a diameter of 1.6 mm. The pore volume having a pore diameter ranging from 20 to 200 nm in the adsorbent B was 0.325 mL/g.

Production Example 3 of an Adsorbent

A 2 L separable flask was charged with 1260 g of ion exchange water, 108 g of $Ni(NO_3)_2.6H_2O$, 13 g of $Cu(NO_3)_2.3H_2O$, 2.4 g of γ-alumina and 2.8 g of 60 percent nitric acid and the mixture was raised to 80° C. with stirring.

A solution obtained by dissolving 30 g of JIS No. 3 water glass and 71 g of $Na_2CO_3$ in 860 g of ion exchange water and by heating the mixture to 80° C. was poured into the flask with stirring. The poured slurry was stirred at 80° C. for one hour and then subjected to filtration and washing with water, followed by drying at 110° C. to obtain a precursor. Then, the precursor was molded into a noodle form by using alumina as a binder, and then, baked, reduced and stabilized to obtain an adsorbent C having a diameter of 1.6 mm. The pore volume having a pore diameter ranging from 20 to 200 nm in the adsorbent C was 0.182 mL/g.

Comparative Production Example 1 of an Adsorbent

An adsorbent D was obtained by carrying out the same preparation method as in Production Example 3 except that the kneading time prior to molding was extended. The pore volume having a pore diameter ranging from 20 to 200 nm in the adsorbent D was 0.095 mL/g.

The metal content, pore volume and mode diameter of pore diameter of the adsorbent A to D obtained in the above Production Examples and Comparative Production Example are collectively shown in Table 1.

Examples 1 and 3 and Comparative Example 1

A fixed-bed reactor was filled with 180 mL of each of the adsorbents A to D. 900 mL/hr (LHSV=5) of the palm kernel oil fatty acid methyl ester obtained in the above Preparation Example and 1900 NL/hr of hydrogen were fed simultaneously, at 20 Mpa at 90° C., at the upper portion of the reactor to carry out an adsorption treatment. The palm kernel oil fatty acid methyl ester was flowed through the reactor in a flow amount 1000 times that of the adsorbent, and then, the palm kernel fatty acid methyl ester flowed afterward was collected. The concentration of residual sulfur in the collected palm kernel fatty acid methyl ester which had been subjected to adsorption treatment and desulfurization activity of the adsorbent are shown in Table 1. The desulfurization activity was calculated according to the following equation.

Desulfurization activity=log (Sulfur concentration before adsorption treatment/Sulfur concentration after adsorption treatment)

Here, "log" indicates natural logarithm.

Example 4 (Production Example of an Alcohol)

Adsorption treatment and hydrogenation reaction of the palm kernel oil fatty acid methyl ester obtained in the above preparation example were continuously carried out by using a fixed-bed reactor. The fixed-bed reactor was provided with two series reactors wherein 360 mL of the adsorbent A was filled in the first reactor and 360 mL of titania-carrying copper-zinc catalyst (composition: Cu=35 percent, Zn=1.8 percent, $TiO_2$ support: 50 percent, 3.2 mmφ×3.2 mm columnar form) was filled in the second reactor. The adsorption condition in the first reactor was designed to be 20 MPa and 90° C. and the flow rate of the palm kernel oil fatty acid methyl ester was 260 mL/h (LHSV=0.72). The concentration of sulfur in the palm kernel oil fatty acid ester after treatment in the first reactor was 0.10 mg/kg.

The hydrogenation reaction condition of the second reactor filled with the hydrogenation catalyst was designed to be as follows: pressure: 20 MPa and temperature: 210° C. The content of alcohols in the obtained solution after the hydrogenation reaction was 96.8 percent when measured using gas chromatography and the saponification value was 4.7 mg-KOH/g.

The invention claim is:

1. A method of producing a fatty acid ester, comprising contacting in a fixed-bed continuous system a starting fatty acid ester with an adsorbent to adsorb sulfur contained in the starting fatty acid ester, the adsorbent comprising at least one metal selected from the group consisting of Ni and Cu in an amount of 10 to 80 percent by weight as a metal oxide(s) thereof per all the adsorbent, having a pore volume having a pore diameter range from 20 to 200 nm within 0.15 to 1.0 mL/g, wherein said absorbent has a molded shape, and wherein said adsorbent is prepared by precipitating a metal and a support simultaneously.

2. The method according to claim 1, wherein the mode diameter of the pore diameter of the adsorbent is from 20 to 200 nm.

3. The method according to claim 1, wherein the adsorbing treatment is carried out in a hydrogen atmosphere.

4. The method according to claim 1, wherein the adsorbing treatment is carried out at from 40 to 200° C.

5. A method of producing an alcohol, comprising hydrogenating a fatty acid ester obtained by the method as claimed in claim 1.

6. The method according to claim 2, wherein the adsorbing treatment is carried out in a hydrogen atmosphere.

7. The method according to claim 2, wherein the adsorbing treatment is carried out at from 40 to 200° C.

8. The method according to claim 3, wherein the adsorbing treatment is carried out at from 40 to 200° C.

9. A method of producing an alcohol, comprising hydrogenating a fatty acid ester obtained by the method as claimed in claim 2.

10. A method of producing an alcohol, comprising hydrogenating a fatty acid ester obtained by the method as claimed in claim 3

11. A method of producing an alcohol, comprising hydrogenating a fatty acid ester obtained by the method as claimed in claim 4.

12. The method according to claim 1, wherein the adsorbent is reduced and activated by hydrogen.

TABLE 1

|  | Example | | | Comparative example |
| --- | --- | --- | --- | --- |
|  | 1 | 2 | 3 | 1 |
| Kind of absorbent | A | B | C | D |
| Content of nickel[*1] (percent by weight) | 76.1 | 62.2 | 63.7 | 63.7 |
| Content of copper[*1] (percent by weight) | — | 8.4 | 7.8 | 7.8 |
| Content of metals (nickel + copper)[*1] (percent by weight) | 76.1 | 70.6 | 71.5 | 71.5 |
| Pore volume having a pore diameter ranging from 20 to 200 nm in the absorbent (mL/g) | 0.361 | 0.325 | 0.182 | 0.095 |
| Mode diameter of pore diameter (nm) | 61 | 50 | 33 | 18 |
| Residual sulfur concentration (mg/kg) | 0.10 | 0.11 | 0.17 | 0.32 |
| Desulfurization activity | 2.30 | 2.21 | 1.77 | 1.14 |

[*1]Content as a metal oxide in the total amount of the absorbent

\* \* \* \* \*